United States Patent [19]

Pihlaja

[11] 4,016,607
[45] Apr. 12, 1977

[54] ARTIFICIAL HAND

[76] Inventor: Eino Pihlaja, 101 Machar Avenue, Thunder Bay P, Ontario, Canada

[22] Filed: July 30, 1976

[21] Appl. No.: 710,028

[52] U.S. Cl. .................................... 3/12; 3/12.7
[51] Int. Cl.² ........................................ A61F 1/06
[58] Field of Search ............ 3/12, 12.5, 12.6, 12.7, 3/12.8; 128/77

[56] References Cited
UNITED STATES PATENTS

| | | | |
|---|---|---|---|
| 1,464,842 | 8/1923 | Burgan | 3/12.6 |
| 2,767,708 | 10/1956 | Keropian | 128/77 |
| 2,867,819 | 1/1959 | George | 3/12.6 |
| 3,434,163 | 3/1969 | Saverino | 3/12 X |
| 3,631,542 | 1/1972 | Potter | 128/77 X |

*Primary Examiner*—Ronald L. Frinks
*Attorney, Agent, or Firm*—Donnelly, Maky, Renner & Otto

[57] ABSTRACT

An artificial hand for a person whose hand stump includes the metacarpus or a portion thereof characterized in the provision of stump and forearm gripping portions which are pivotally connected together on opposite sides of the wrist for up and down pivotal movement of the stump about the corresponding axis of the wrist, said forearm gripping portion including a detachable thumb-like forward projection from either or each side thereof (for use on the left or right forearm), and said stump gripping portion having forwardly extending curved fingers which, upon pivotal movement of the stump-gripping portion enables receiving and gripping of various objects between the fingers and the forward projection or projections. The artificial hand herein is further characterized in that the aforesaid pivots also permit lateral pivoting of the stump gripping portion and fingers thereof.

11 Claims, 4 Drawing Figures

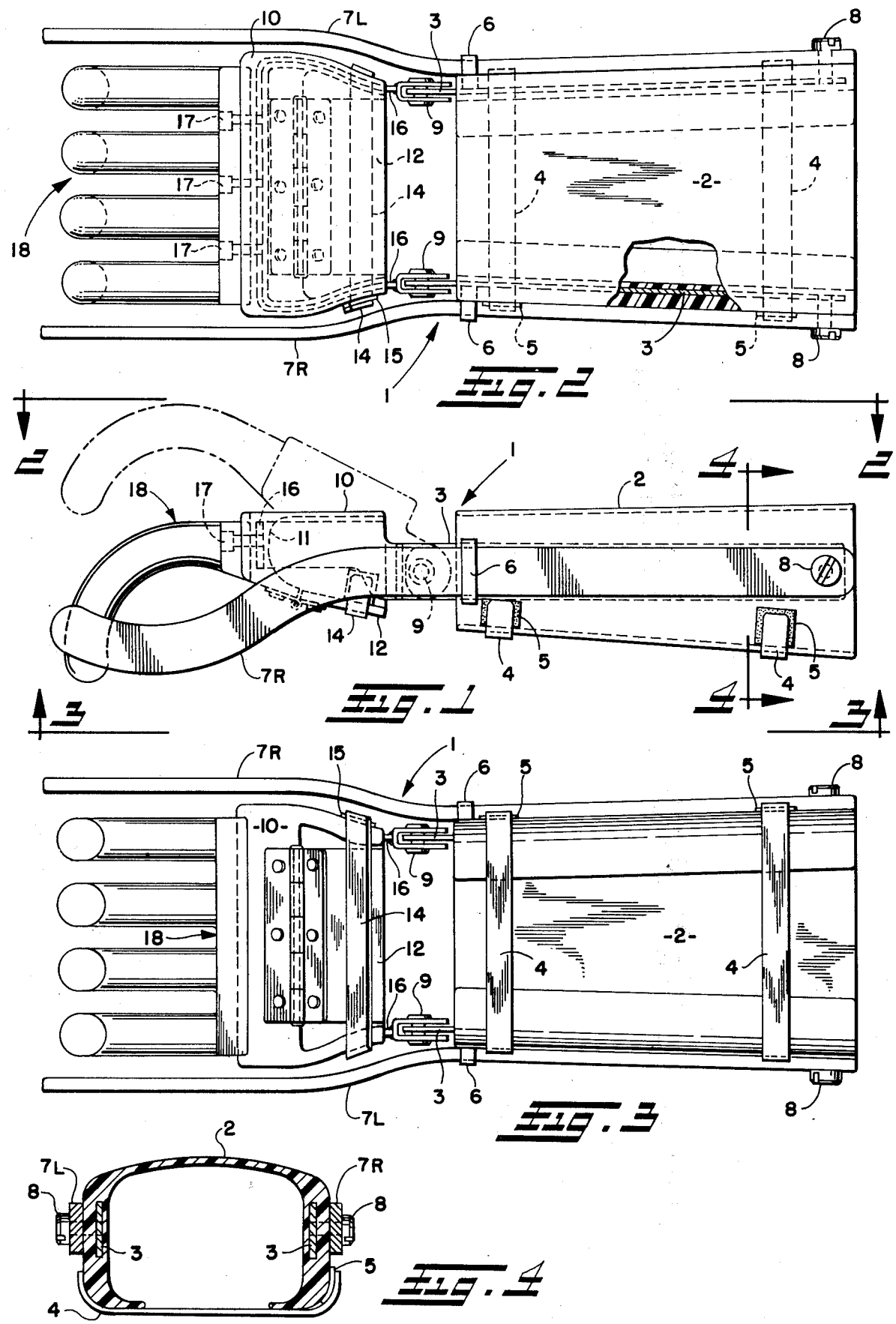

ARTIFICIAL HAND

BACKGROUND OF THE INVENTION

In most instances, hand amputations are done at or above the wrist and hence to provide wrist action on the artificial hand it is necessary to employ complex cable and like arrangements responsive to arm, elbow, or shoulder movements.

SUMMARY OF THE INVENTION

An artificial hand which when fastened on the forearm into metacarpus gripping position provides either or both a left-hand and righthand forwardly extending thumb-like portion with respect to which curved fingers are opened and closed by movement of the metacarpus about pivots on opposite sides of the forearm gripping portion which correspond generally to the wrist pivot.

It is an object of this invention to provide an artificial hand of the character indicated by which the up and down movement of the metacarpus enables gripping and releasing a wide variety of sizes and types of articles.

It is another object of this invention to provide pivots as aforesaid which additionally provide for lateral pivoting of the metacarpus and fingers thereof.

Other objects and advantages will appear from the ensuing description.

BRIEF DESCRIPTION OF THE DRAWING

FIG. 1 is a side elevation view of an artificial hand embodying the present invention;

FIGS. 2 and 3 are respectively top and bottom plan views of the artificial hand as viewed along the respective lines 2—2 and 3—3 of FIG. 1; and FIG. 4 is a transverse cross-section view as viewed along the line 4—4, FIG. 1.

DETAILED DESCRIPTION OF A PREFERRED EMBODIMENT

The artificial hand 1 herein shown comprises a forearm gripping portion 2 as of flexible plastic material having stainless steel or like inserts 3 on opposite sides thereof which project forwardly from opposite sides of said forearm gripping portion 2. Said forearm gripping portion 2 is adjustably clamped on the forearm as by means of flexible straps 4 having fastener means which cooperate with fastener means 5 on the forearm gripping portion 2. To provide for quick and easy fastening and releasing of the forearm gripping portion, the cooperating fastener means may comprise Velcro strips.

The front portion of the forearm gripping portion 2 has loop members 6 affixed to opposite sides thereof through which an elongated member 7R and/or 7L may be positioned for attachment to the forearm gripping portion 2 by the screw 8 which has threaded engagement with the respective insert 3. Said members 7R and/or 7L when installed as aforesaid, project forwardly of the forearm gripping portion 2 and are shaped as best shown in FIGS. 1, 2 and 3 to correspond with right and lefthand thumbs to enable the forearm gripping portion 2 to be used in connection with either the left or right forearm, said forwardly projecting thumb-like portions 7R and 7L when both installed providing as hereinafter explained in detail laterally-spaced supports for an article to be gripped by the artificial hand.

Pivotally mounted at 9 to the forwardly projecting portions of the inserts 3 is a metacarpus gripping portion 10 which is formed with a socket 11 to receive the metacarpus. A gripping flap 12 hinged to the bottom of said member and adjustably fastened by a strap 14 having fastener means cooperating with fastener means 15 such as Velcro strips as described in connection with the forearm gripping portion 2. The metacarpus gripping portion 10 is also preferably formed of flexible plastic with a stainless steel or like reinforcement member 16 which projects rearwardly to form the pivotal connections 9 on opposite sides of the wrist.

Detachably connected to the metacarpus gripping portion 10 as by the screws 17 having threaded engagement with the reinforcement member 16 is a replaceable finger unit 18 including four fingers which are curved toward the thumb-like portions 7R and 7L as best shown in FIG. 1.

In the use of the artificial hand 1 it is preferred that a heavy sock be slipped over the metacarpus, wrist, and forearm for comfort (to obviate the need of providing padding within the metacarpus and forearm gripping portions 10 and 2 of the artificial hand 1). The stump, wrist, and forearm are inserted into the artificial hand 1 from the large end of the forearm gripping portion 2 until the metacarpus abuts bottom of socket 11 whereupon the straps 4 and 14 may be adjustably fastened.

It can be seen that by moving the metacarpus up and down about the axis of the pivots 9 which correspond to the wrist pivot, the artificial hand 1 may be opened and closed to receive an article to be gripped and to grip the article between the curved fingers 18 and the concavely curved portion or portions of the spaced-apart thumb-like portion 7R or 7L or thumb-like portions 7R and 7L.

The wrist pivots 9 are preferably made with substantial looseness so that the metacarpus may swing laterally with respect to the forwardly extending thumb-like portions 7R or 7L or laterally between 7R and 7L. If desired, the artificial hand 1 herein may be used with one thumb-like portion 7R or 7L removed in which case the hand 1 would more closely resemble the natural left or right hand.

Preferably, the curved fingers are hollow for weight saving and as apparent said finger unit 18 may be made of plastic material or of lightweight metal such as aluminum or aluminum alloy and, of course, for added strength the finger unit 18 may be made of stainless steel or like strong metal. Likewise, the forwardly extending portions 7R and 7L from the forearm gripping unit 2 may be made of materials as described in connection with the finger unit. In any case, in the event of damage to the forwardly extending portions 7R and 7L, the damaged one may be quickly replaced simply by removing the associated screw 8 and slipping the damaged one forwardly out of engagement with its loop 6 and inserting a new one in its place. Similarly, in the event of damage to the finger unit 18, the screws 17 are removed and a new finger unit 18 installed.

The embodiments of the invention in which an exclusive property or privilege is claimed are defined as follows:

1. An artificial hand for an amputee having at least a portion of the metacarpus comprising a forearm gripping portion and a metacarpus gripping portion which are pivotally connected together on opposite sides to define pivots for positioning along opposite sides of the wrist; said forearm gripping portion having affixed on one side thereof a forwardly projecting thumb-like member; said metacarpus gripping portion having forwardly projecting curved finger-like members which upon movement of the metacarpus gripping portion about said pivots opens and closes said finger-like members with respect to said thumb-like member for respectively receiving and gripping an object therebetween.

2. The artificial hand of claim 1 wherein the other side of said forearm gripping portion has another thumb-like forwardly projecting member whereby an article supported by both thumb-like members may be firmly and stably gripped by said finger-like members.

3. The artificial hand of claim 1 wherein said pivots provided for lateral swinging movement of said metacarpus gripping portion and finger-like members toward or away from said thumb-like member.

4. The artificial hand of claim 2 wherein said pivots provide for lateral swinging movement of said metacarpus gripping portion and finger-like members between said thumb-like members.

5. The artificial hand of claim 1 wherein said forearm gripping portion has means for detachably securing said thumb-like member to one side thereof.

6. The artificial hand of claim 1 wherein said finger-like members are interconnected together; and wherein said metacarpus gripping portion has means for detachably connecting the interconnected finger-like members thereto.

7. The artificial hand of claim 1 wherein said forearm gripping portion is shaped to extend over the top and sides of the forearm and is curved partway along the underside with strap and fastener means thereacross to adjustably secure the forearm gripping portion into gripping engagement with the amputee's forearm.

8. The artificial hand of claim 1 wherein said metacarpus gripping portion forms a socket to receive the metacarpus, said socket having a gripping flap hinged thereto for engaging with the palm portion of the metacarpus.

9. The artificial hand of claim 8 wherein strap and fastener means adjustably secures said flap in metacarpus gripping position.

10. The artificial hand of claim 1 wherein said thumb-like member is retained by a loop adjacent the front portion of said one side of said forearm gripping portion and extends to the rear portion of said one side whereat it is secured by screw means.

11. The artificial hand of claim 10 wherein the front portion of the other side of said forearm gripping portion has a similar loop to receive a thumb-like member corresponding to the thumb of the other hand, said other side at its rear portion having provision for screw attachment of the last-mentioned thumb-like member.

* * * * *